(12) United States Patent
Kydonieus et al.

(10) Patent No.: US 12,226,534 B2
(45) Date of Patent: Feb. 18, 2025

(54) TRANSDERMAL PACKAGING MEMBRANES

(71) Applicant: Agile Therapeutics, Inc., Princeton, NJ (US)

(72) Inventors: Agis Kydonieus, Kendall Park, NJ (US); C. Gregory Arnold, Kinnelon, NJ (US); Robert G. Conway, Whitehouse Station, NJ (US); Thomas M. Rossi, Portsmouth, NH (US)

(73) Assignee: Agile Therapeutics, Inc., Princeton, NJ (US)

( * ) Notice: Subject to any disclaimer, the term of this patent is extended or adjusted under 35 U.S.C. 154(b) by 0 days.

(21) Appl. No.: 16/315,257

(22) PCT Filed: Jul. 5, 2017

(86) PCT No.: PCT/US2017/040749
§ 371 (c)(1),
(2) Date: Jan. 4, 2019

(87) PCT Pub. No.: WO2018/009565
PCT Pub. Date: Jan. 11, 2018

(65) Prior Publication Data
US 2019/0160020 A1 May 30, 2019

Related U.S. Application Data

(60) Provisional application No. 62/358,956, filed on Jul. 6, 2016.

(51) Int. Cl.
| | | |
|---|---|---|
| A61K 9/70 | (2006.01) |
| A61J 1/00 | (2023.01) |
| A61K 31/565 | (2006.01) |
| A61K 31/567 | (2006.01) |
| A61K 47/12 | (2006.01) |
| A61K 47/14 | (2017.01) |
| B32B 5/18 | (2006.01) |
| B32B 7/06 | (2019.01) |
| B32B 7/12 | (2006.01) |
| B32B 15/085 | (2006.01) |
| B32B 15/09 | (2006.01) |
| B32B 15/20 | (2006.01) |
| B32B 27/00 | (2006.01) |
| B32B 27/06 | (2006.01) |
| B32B 27/08 | (2006.01) |
| B32B 27/10 | (2006.01) |
| B32B 27/28 | (2006.01) |
| B32B 27/30 | (2006.01) |
| B32B 27/32 | (2006.01) |
| B32B 27/36 | (2006.01) |
| B32B 27/40 | (2006.01) |
| A61K 47/20 | (2006.01) |

(52) U.S. Cl.
CPC ............... *A61K 9/7038* (2013.01); *A61J 1/00* (2013.01); *A61K 31/565* (2013.01); *A61K 31/567* (2013.01); *A61K 47/12* (2013.01); *A61K 47/14* (2013.01); *B32B 5/18* (2013.01); *B32B 7/06* (2013.01); *B32B 7/12* (2013.01); *B32B 15/085* (2013.01); *B32B 15/09* (2013.01); *B32B 15/20* (2013.01); *B32B 27/00* (2013.01); *B32B 27/065* (2013.01); *B32B 27/08* (2013.01); *B32B 27/10* (2013.01); *B32B 27/28* (2013.01); *B32B 27/30* (2013.01); *B32B 27/304* (2013.01); *B32B 27/306* (2013.01); *B32B 27/32* (2013.01); *B32B 27/322* (2013.01); *B32B 27/325* (2013.01); *B32B 27/36* (2013.01); *B32B 27/40* (2013.01); *A61K 47/20* (2013.01); *B32B 2250/05* (2013.01); *B32B 2255/10* (2013.01); *B32B 2255/26* (2013.01); *B32B 2266/025* (2013.01); *B32B 2266/08* (2013.01); *B32B 2307/54* (2013.01); *B32B 2307/7244* (2013.01); *B32B 2307/7246* (2013.01); *B32B 2307/748* (2013.01); *B32B 2405/00* (2013.01); *B32B 2439/80* (2013.01); *B32B 2556/00* (2013.01)

(58) Field of Classification Search
CPC .............. A61K 2300/00; A61K 31/565; A61K 31/567; A61K 47/12; A61K 47/14; A61K 47/20; A61K 9/7038; B32B 27/00; B32B 15/085; B32B 15/09; B32B 15/20; B32B 2250/05; B32B 2255/10; B32B 2255/26
USPC .......................................................... 424/449
See application file for complete search history.

(56) References Cited

U.S. PATENT DOCUMENTS

| | | | |
|---|---|---|---|
| 5,240,525 A * | 8/1993 | Percec | B32B 27/08 156/244.11 |
| 8,246,978 B2 | 8/2012 | Kydonieus et al. | |

(Continued)

FOREIGN PATENT DOCUMENTS

WO    WO-02026494 A3 *    8/2002    ............ B32B 27/32

OTHER PUBLICATIONS

Corresponding International Search Report and Written Opinion in PCT/US2017/040749, mailed Sep. 22, 2017.

*Primary Examiner* — Zohreh A Fay
(74) *Attorney, Agent, or Firm* — Seed IP Law Group LLP

(57) ABSTRACT

Article side polymers useful in the packaging of transdermal patches are disclosed. These films do not absorb skin permeation enhancers that are contained in transdermal patches including keto acids such as levulinic acid or sulfoxides such as an alkyl sulfoxide, e.g., dimethyl sulfoxide. Using such polymeric film, multilayer pouch constructions can be manufactured which include other polymeric layers, such as aluminum foil for moisture and oxygen barrier properties, polyester for tear resistance and paper layers for optimal printing and design.

19 Claims, No Drawings

(56) References Cited

U.S. PATENT DOCUMENTS

| | | |
|---|---|---|
| 2004/0053901 A1 | 3/2004 | Chien |
| 2010/0292660 A1 | 11/2010 | Kydonieus |
| 2014/0178459 A1* | 6/2014 | Kisak .................... A61K 47/14 |
| | | 424/449 |
| 2015/0258757 A1 | 9/2015 | Ishizaki et al. |

* cited by examiner

TRANSDERMAL PACKAGING MEMBRANES

FIELD OF THE INVENTION

The invention relates to the field of transdermal delivery systems. In particular, materials useful in the packaging of transdermal patches are disclosed.

BACKGROUND OF THE INVENTION

There are over 20 drugs being administered transdermally, such as nitroglycerine, nicotine, fentanyl, estradiol, scopolamine, clonidine, selegiline and rivastimine among others. The patches are applied adhesively to the skin and the drug is delivered through the skin by diffusion through a thermodynamic gradient from the patch through the skin, the extracellular matrix and into the blood. All transdermal patches are packaged in a pouch which is opened by the patient, who removes the patch and applies it to the skin. The packaging material is typically a multilayered film which is heat sealed to itself to form a container within which resides the transdermal patch. The package formed is of critical importance since the patch will have to remain in the package up to two years, which is the usual useful storage life of a transdermal product. Therefore the package should protect the patch, the drug as well as the excipients, including skin permeation enhancers, from contamination, moisture, oxygen, sunlight and microbes.

The absorption of drugs, enhancers and other excipients into the polymer layers of the packaging films is a much more difficult issue. Dissolution of these substances into polymers depends on their physical and other properties, such as, e.g., their structure including polarity, molecular weight, branching, degree of crosslinking and crystallinity.

Patches that comprise as skin permeation enhancers a keto acid and a long chain monoglyceride or a C8-C16 ester of a short chain carboxylic acid, specifically, levulinic acid and glycerol monooleate or lauryl lactate are described in U.S. Pat. No. 9,144,553. Patches that comprise as skin permeation enhancers a sulfoxide and a C8-C16 ester of a short chain carboxylic acid, a lower alkyl ester of a short chain carboxylic acid, and a medium chain fatty acid, specifically, dimethyl sulfoxide, lauryl lactate, ethyl lactate, and capric acid, are described in U.S. Pat. No. 7,384,650.

SUMMARY OF THE INVENTION

The invention pertains to obtaining an article side polymeric film that is not able to absorb skin permeation enhancers that are contained in a transdermal patch, the enhancers comprising a keto acid such as levulinic acid or a sulfoxide such as an alkyl sulfoxide, e.g., dimethyl sulfoxide. (An article side polymeric film is a film that forms the innermost liner of a pouch, or envelope, for storing a transdermal patch.) Using such polymeric film, multilayer pouch constructions can be manufactured which include other polymeric layers, such as aluminum foil for moisture and oxygen barrier properties, polyester for tensile strength and paper layers for optimal printing and design.

Illustrative embodiments of this invention include, without limitation, a pouch or other container for storing a transdermal delivery patch comprising an active pharmaceutical ingredient and (i) at least one skin penetration enhancer that is a keto acid and at least one additional enhancer such as a long chain monoglyceride or a C8-C16 ester of a short chain carboxylic acid, or (ii) at least one skin penetration enhancer that is a sulfoxide, wherein the pouch comprises a multilayered packaging film comprising an article side polymer layer selected from a fluoropolymer, polypropylene, polyethylene terephthalate, a low density polyethylene (LDPE), a cyclic olefin copolymer, or polyacrylonitrile/methyl acrylate-acrylonitrile/butadiene graft copolymer.

In an example of such illustrative embodiment comprising levulinic acid, the additional enhancers comprise glycerol monooleate or lauryl lactate.

In an example of such illustrative embodiment comprising a sulfoxide, the sulfoxide is DMSO and the additional enhancer comprises a C8-C16 ester of a short chain carboxylic acid (such as lauryl lactate) or a lower alkyl ester of a short chain carboxylic acid (such as ethyl lactate).

In a further example of such illustrative embodiment comprising a sulfoxide, the sulfoxide is DMSO and the additional enhancer comprises a C8-C16 ester of a short chain carboxylic acid (such as lauryl lactate), a lower alkyl ester of a short chain carboxylic acid (such as ethyl lactate), and a medium chain fatty acid (such as capric acid).

In a further example of such illustrative embodiment, the patch comprises a polymeric matrix as described in U.S. Pat. No. 9,144,553 or as described in U.S. Pat. No. 7,384,650.

Such illustrative embodiments of this invention comprise a pouch for storing a transdermal delivery patch, the patch comprising a backing layer affixed to an adhesive polymer matrix, wherein the adhesive polymer matrix comprises:
 a. an active pharmaceutical ingredient;
 b. an adhesive polymer; and
 c. (i) a first penetration enhancer selected from the group consisting of a keto acid and a pharmaceutically acceptable salt thereof and a second penetration enhancer selected from the group consisting of long chain monoglycerides and C8-C16 esters of short chain carboxylic acid; or
 (ii) a first penetration enhancer selected from the group consisting of alkyl sulfoxides and a second penetration enhancer selected from the group consisting of C8-C16 esters of a short chain carboxylic acid, lower alkyl esters of a short chain carboxylic acid, or both;
wherein the pouch comprises a multilayered packaging film comprising an article side polymer layer selected from a fluoropolymer, polypropylene, polyethylene terephthalate, a low density polyethylene (LDPE), a cyclic olefin copolymer, or polyacrylonitrile/methyl acrylate-acrylonitrile/butadiene graft copolymer.

In an illustrative embodiment of such pouch, the invention comprises a pouch for storing a transdermal delivery system, the system comprising a backing layer affixed to an adhesive polymer matrix, wherein the adhesive polymer matrix comprises:
 a. levonorgestrel or levonorgestrel and ethinyl estradiol,
 b. an adhesive polymer; and
 c. about 0.5% to about 10% of a first penetration enhancer selected from the group consisting of levulinic acid and a pharmaceutically acceptable salt thereof and about 0.5% to about 10% of a second penetration enhancer selected from the group consisting of glyceryl monooleate and lauryl lactate;
wherein the pouch comprises a multilayered packaging film comprising an article side polymer layer selected from a fluoropolymer, polypropylene, polyethylene terephthalate, a low density polyethylene (LDPE), a cyclic olefin copolymer, or polyacrylonitrile/methyl acrylate-acrylonitrile/butadiene graft copolymer.

In another illustrative embodiment of such pouch, the invention comprises a pouch for storing a transdermal delivery system, the system comprising a backing layer affixed to an adhesive polymer matrix, wherein the adhesive polymer matrix comprises:

a. levonorgestrel or levonorgestrel and ethinyl estradiol,
b. an adhesive polymer; and
c. about 4% to about 12% of dimethyl sulfoxide, about 4% to about 13% of a fatty (C8-C16) alcohol ester of lactic acid, about 0.5% to about 2.5% of a lower (C1-C4) alkyl ester of lactic acid; and from about 3% to about 9% of a medium chain fatty acid;

wherein the pouch comprises a multilayered packaging film comprising an article side polymer layer selected from a fluoropolymer, polypropylene, polyethylene terephthalate, a low density polyethylene (LDPE), a cyclic olefin copolymer, or polyacrylonitrile/methyl acrylate-acrylonitrile/butadiene graft copolymer.

The percent (%) amounts recited herein are percents by weight, also referred as wt % (or w/w) of the active portion of the transdermal patch, i.e., they are the final percentages by weight of the adhesive polymer matrix after fabrication of the system.

Embodiments of the invention include the pouch described herein containing a transdermal delivery device (patch) as well as the pouch without the transdermal patch.

DETAILED DESCRIPTION OF EMBODIMENTS OF THE INVENTION

Transdermal patches include, e.g., drug in adhesive patches, other adhesive matrix patches, reservoir patches, vapor patches and other transdermal drug delivery systems in which there is the potential for excipients or active pharmaceutical ingredients to be absorbed by polymer films used in a pouch for storing the transdermal patches.

A transdermal patch comprising as skin permeation enhancers, as described, e.g., in U.S. Pat. No. 9,144,553 or U.S. Pat. No. 7,384,650, will require a pouch or other container for storage having an article side polymer layer that does not significantly absorb volatilized enhancers during storage. The pouch preferably absorbs less than 0.5% by weight of the skin permeation enhancer(s) during a storage period of 6 months or longer at room temperature, preferably 12 months or longer, most preferably 24 months or longer.

The article side polymer film is disposed on the inside surfaces of the pouch or other container and is sealed around the edges to enclose the pouch or other container. Such pouch or other container can comprise additional polymeric or other films disposed on the non-article sides of the article side polymer films.

The adhesive polymer in matrix type patches is generally a polymeric pressure sensitive adhesive (PSA) and is generally a polyacrylate PSA, a polyisobutylene PSA, or a silicone PSA. Illustrative examples are described, e.g., in U.S. Pat. No. 8,246,978.

For purposes of describing this invention, a long chain monoglyceride is a glycerol in which one of the —OH groups has formed an ester with a long chain fatty acid. The ester bond is generally in the 1 position but 2-monoacylglycerols are not excluded. Examples include glycerol monooleate and glycerol monostearate.

A long chain fatty acid is a saturated or unsaturated C15-C21 fatty acid. Long chain fatty acids are generally linear, i.e., unbranched, and unsubstituted, but branched or substituted derivatives are not excluded. C16 to C20 fatty acids, particularly C18 fatty acids, are preferred for the practice of this invention. Examples include oleic acid and stearic acid.

A keto acid is a short chain carboxylic acid having one or two =O substituents. Examples include pyruvic acid, acetoacetic acid, and levulinic acid.

A medium chain fatty acid ester is a medium chain fatty acid ester of a short chain carboxylic acid. An example is lauryl lactate (LL).

A medium chain fatty acid is a saturated or unsaturated C6-C14 fatty acid. Medium chain fatty acids are generally linear, i.e., unbranched, and unsubstituted, but branched and substituted derivatives are not excluded. C10 to C14 fatty acids, particularly C12 fatty acids, are illustrative. Examples include capric acid and lauric acid.

A short chain carboxylic acid is a C2-C5 carboxylic acid. Hydroxy acids, e.g., alpha-hydroxy acids, are included. Examples include propionic acid, valeric acid, and butyric acid, and the hydroxy acids, lactic acid and glycolic acid.

A lower alkyl group is a C1-C4 alkyl group, saturated or unsaturated, i.e., methyl, ethyl, ethenyl, propyl, propenyl, butyl, and butenyl.

For the avoidance of doubt, levulinic acid is a keto acid; glycerol monooleate is a long chain monoglyceride; lauryl lactate is a C8-C16 ester of a short chain carboxylic acid; ethyl lactate is a lower alkyl ester of a short chain carboxylic acid; capric acid is a medium chain fatty acid.

Useful article side polymer layers are fluoropolymer, polypropylene, polyethylene terephthalate, a low density polyethylene, a cyclic olefin copolymer, or polyacrylonitrile/methyl acrylate-acrylonitrile/butadiene graft copolymer films.

Non-limiting examples of fluoropolymers include polychlorotrifluoroethylene (e.g., Aclar® PCTFE) (Honeywell, Morris Plains, New Jersey), perfluoro copolymer of tetrafluoroethylene and hexafluoropropylene (e.g., Neoflon™ FEP) (Daikin, Osaka), copolymer of ethylene and tetrafluoroethylene (e.g., Neoflon™ ETFE) (Daikin, Osaka), fluorinated ethylene-propylene, and polyvinyl fluoride.

A non-limiting example of a polyacrylonitrile/methyl acrylate-acrylonitrile/butadiene graft copolymer is Barex® 210 acrylonitrile-methyl acrylate copolymer (INEOS Barex, League City, Texas).

A non-limiting example of a cyclic olefin copolymer is an ethylene-norbornene copolymer.

The active pharmaceutical ingredient (API) can be any drug that is deliverable transdermally. One embodiment is a contraceptive patch in which the API is a progestin or a progestin in combination with an estrogen. Progestins include gestodene, dienogest, drospirenone, levonorgestrel, cyproteronacetate, tetrahydrodienogest, norethisterone, norethisteronacetate, desogestrel, 3-keto-desorgestrel, norgestimate, lynestrenol, medroxyprogesterone acetate, norgestrel, norethisteroneenanthate, trimegestone or alpha and beta-progesterone receptor ligands. Estrogens include 17-β estradiol and ethinyl estradiol.

When the API is a progestin or a progestin and an estrogen, the transdermal patch can deliver a contraceptive amount of the API during a seven day wear period.

Unless otherwise indicated, examples of specific embodiments described herein are offered without limitation.

The examples that follow demonstrate differential absorption of enhancers by certain types of polymeric films.

EXAMPLES

Example 1

Early in the development process of a contraceptive patch containing levonorgestrel and ethinyl estradiol, prototype patch formulations containing the four enhancers mentioned above were packaged in a five-layer heat sealed pouch material constructed from polyester, aluminum foil and low-density polyethylene (inner layer). In a two year stability study, it was observed that this packaging closure system was not able to prevent the loss of the enhancers over the course of the intended shelf life of the product. When stored in this packaging system, up to 44% of DMSO and 39% of EL was lost from the product over the course of 24 months at 25° C./60% RH. This study revealed the fact that a polyethylene liner is not an appropriate inner layer choice for containment of the enhancers contained in this contraceptive patch.

The root cause of this loss of volatile enhancers was theorized to be evaporation of the enhancers from the adhesive drug matrix, migration into the head space of the pouch, and subsequent absorption into the polyethylene liner. Thus polyethylene and ethylene vinyl acetate polymers that are most commonly used to package transdermal products are not appropriate for a patch containing the enhancers.

Example 2 Through 15

Polymeric samples were obtained from different vendors and tested as far as their ability to prevent absorption of the enhancers, dimethyl sulfoxide, ethyl lactate, lauryl lactate and decanoic acid. The samples tested included polymeric films that could be used as active side layers of packaging films (e.g. polypropylene, polyester and acrylonitrile/methyl acrylate-acrylonitrile/butadiene graft copolymer) to be used with transdermal patches containing these enhancers, as well as multilayered films containing some of the monolayers mentioned above as well as other layers. In addition different other polymeric films, adhesives, foams and laminates were tested to determine if other polymeric films were able to minimize the absorption of the above mentioned enhancers.

Samples of the 14 mentioned polymeric films, adhesives, foams and laminates mentioned above were weighed accurately to five decimal places and placed in a stainless steel desiccator. On the bottom of the desiccator were placed 5 grams of the four enhancers DMSO, lauryl lactate, ethyl lactate and decanoic acid in the ratio of about 8 to 8 to 2 to 6. The samples were placed in a 40 degree Centigrade oven and removed from the desiccator and weighed at the time intervals shown in Table 1. The amount of enhancers absorbed was determined by subtraction of the zero time reading from that of any specific time reading. The values are shown in the Table 1 as percentage of enhancers absorbed per unit sample weight. It is obvious from the data that the heat seal layer polymers, polypropylene, polyester (Polyethylene terephthalate-PET-crystalline), and acrylonitrile/methyl acrylate-acrylonitrile/butadiene graft copolymer and laminates comprising these polymers have low absorption of the enhancers. The polymers, polyethylene, polyurethane, polyvinyl chloride, and ethylene vinyl acetate copolymer (PVA) show high absorption of enhancers. Pressure sensitive adhesives such as acrylates and polyisobutylene show high enhancer absorption. Crystalline polyester does not seat to itself (see US patent application 2010/0292660 where ultrasonic welding was developed in an attempt to address the heat seal issue of crystalline polyester), so it is not a primary candidate as an active side membrane in a multilayered packaging laminate. Therefore, polypropylene and the acrylonitrile/methyl acrylate-acrylonitrile/butadiene graft copolymer are the only two active side membranes experimentally determined to be appropriate for the four enhancer system mentioned above.

TABLE 1

Enhancer Absorption into Polymeric Films, Laminates, Adhesives and Foams

| Sample Description | Excipient Absorption (%) Time in Days | | | | |
|---|---|---|---|---|---|
| | 3 | 7 | 30 | 56 | 90 |
| 1. Polypropylene Film, 2 mil (a) | 0.11 | 0.25 | 0.035 | 0.73 | 1.58 |
| 2. Polyester Film, 1 mil (b) | 0.06 | 0.12 | 0.18 | 0.23 | 0.58 |
| 3. Acrylonitrile/Methyl Acrylate acrylonitrile butadiene copolymer Film (Barex 210) (c) | −0.3 | −0.06 | −0.14 | −0.04 | −0.07 |
| 4. Polyester Film (1 mil) coated With Silicone (d) | 0.00 | 0.05 | 0.11 | 0.11 | 0.27 |
| 5. Melt blown Polyurethane Non- woven (e) | 0.93 | 1.98 | 3.95 | 3.35 | 4.65 |
| 6. Ethylene/Butylene/Ethylene Copolymer on Polyester film (f) | 1.91 | −0.69 | 4.21 | 5.72 | 6.61 |
| 7. Polyester/Foil/Polypropylene Laminate (g) | 0.01 | 0.03 | 0.12 | 0.22 | 0.49 |
| 8. Polyester/Foil/Polyethylene Laminate (h) | 0.2 | 1.75 | 3.1 | 3.97 | 5.23 |
| 9. Polyester/Foil/Acrylonitrile/methyl acrylate acrylonitrile/butadiene graft copolymer laminate (i) | −0.19 | −0.09 | −0.04 | 0.03 | 0.09 |
| 10. Polyester Film coated with 3 mil Poliyisobutylene adhesive (J) | −0.44 | −0.04 | 0.78 | 0.87 | 1.61 |
| 11. Polyurethane film coated with Acrylic adhesive (k) | 1.45 | 2.57 | 4.62 | 4.37 | 6.08 |
| 12. Polyester non-woven coated with Acrylic adhesive (l) | 0.68 | 1.35 | 2.39 | 2.32 | 3.29 |
| 13. Polyethylene/EVA crosslinked Copolymer closed cell foam (m) | 0.05 | 0.2 | 0.32 | 0.44 | 0.73 |
| 14. Polyvinyl Chloride coated foam medical tape (n) | 0.75 | 1.57 | 3.15 | 2.95 | 4.16 |

Samples provided: Amcor (a), (c), (g), (i); 3M (e), (k), (l), (n); Hercon Labs (b), (d), (h); Kraton Company (f); Sekisui Voltek (m)

Example 16

As mentioned above, crystalline polyester is not an appropriate active side layer because it does not heat seal to itself, which is important for an active side polymer layer. There is however extensive literature indicating that polyester can be made amorphous by appropriate processing conditions. For example U.S. Pat. No. 3,745,150 states "Therefore, it can be said that in the art of producing polyethylene terephthalate film, processes are known that result in either a crystalline or amorphous film". The inventors tested two amorphous polyethylene terephtalate (APET) polymers films together with a crystalline polyethylene terephthalate (PET-polyester). The experiment was similar to the desiccator experiment discussed in examples 1-14. The results are shown in Table 2. The data as presented in Table 2 shows that although there was substantial variability at the different time points studied, it appears that the absorption of the four enhancers was similar between the crystalline and amorphous polyethylene terephthalate films and therefore the amorphous films can be used as article side films in multilayered laminates for packaging transdermal products containing the four enhancers of our invention as well as their derivatives and congeners.

TABLE 2

Enhancer Absorption into Crystalline and Amorphous Polyester Films

| Sample Description | Excipient Absorption (%) Time in Days | | | | |
|---|---|---|---|---|---|
| | 3 | 7 | 14 | 31 | 60 |
| 118 gauge APET film | 0.39 | 0.68 | 1.03 | 0.82 | 0.82 |
| 110 gauge APET film | 1.14 | 0.99 | 1.33 | 1.24 | 1.21 |
| 92 gauge PET film | −.02 | 0.23 | 0.09 | 0.67 | 0.74 |

Example 17

Fluoropolymers are polymers with multiple strong carbon-fluorine bonds. It is generally known that they have good resistance to acids and bases as well as to different solvents. They can be thermoset or thermoplastic, but in general they are available as films. Examples of fluoropolymers include polyvinyl fluoride, polytetrafluoroethylene, polychlorotrifluoroethylene, perfluoroalkoxy polymer, fluorinated ethylene-propylene, polyvinylidenefluoride, polyethylenetetrafluoroethylene, chlorotrifluoroethylenevinylidenefluoride, perfluoropolyether and perfluorosulfonic acid among others. The procedure mentioned above in examples 1-14 was repeated in this experiment, using a 1.5 mil thick fluoropolymer film made of polychlorotrifluoroethylene (Aclar). The sample was placed in a desiccator at 40 degree Centigrade oven and tested for absorption of the enhancers at the time points of 3, 7, 30, 60 and 90 days. No absorption was detected at any of the time points. Therefore thermoplastic fluoropolymers are appropriate to be used as the active side polymer in multilayered packaging structures for transdermal patches containing the above mentioned enhancers, their derivatives and congeners.

Example 18

Transdermal patches containing levonorgestrel and ethinyl estradiol and four enhancers, DMSO, Lauryl Lactate, Ethyl lactate and decanoic acid (75 milligrams at an approximate ratio of 8 to 8 to 2 to 6) were placed in a stability oven at the accelerated conditions of 40 degrees Centigrade for a period of six months. The rule of thumb is that stability-wise three months at 40 degrees Centigrade is equivalent to 18 months at room temperature. The packaging film used to contain the transdermal patches had an active side layer of acrylonitrile/methyl acrylate-acrylonitrile/butadiene graft copolymer. After 6 months at the above mentioned conditions the patches were removed from the stability oven, the packaging film cut into small pieces and the total sample extracted with 10 ml of THF by shaking on a wrist action shaker for about 20 hours. Using Gas Chromatographic techniques the amount of the four enhancers absorbed in the packaging film were determined. There was no DMSO, ethyl lactate and decanoic acid detected and only 0.2 milligrams of lauryl lactate.

Example 19

Transdermal patches as shown in Example 16 were obtained and tested for the amount of the four enhancers mentioned in Example 16 that had absorbed in the release liner of the transdermal patch. The release liner was composed of crystalline polyester coated with silicone release polymer (this is the same polymer composition as shown in example 4 above). The release liner was peeled from the patch, cut into small pieces and extracted with 5 ml of THF by shaking on a wrist action shaker for 20 hours. Using the same Gas Chromatography methods as in Example 16, the amount of the four enhancers absorbed into the crystalline polyester release liner were determined. There was no ethyl lactate detected in the release liner and only 0.02 milligrams of lauryl lactate, 0.03 milligrams of decanoic acid and 0.56 milligrams of DMSO.

Example 20

It is a key parameter of the active side membranes of packaging films that they adhere to themselves under appropriate heat and temperature conditions. Ten of the above mentioned structures were heat sealed to themselves using a bench top heat sealing unit. Different temperature, pressure and dwell time was required to properly heat seal the different structures. The heat seal conditions ranged from 225 to 400 degrees F., 40 to 90 psi of pressure, with dwell times of between 0.5 and 1.5 seconds. Twelve samples of each structure were tested for heat seal strength. In all samples a destruction of the seal was obtained, indicating that the heat seal was stronger than that of the material itself. The force in grams required to break the seal was between 1000 and 5000.

The present invention is not limited to the embodiments described and exemplified above, but is capable of variation and modification within the scope of the appended claims. Published literature, including but not limited to patent applications and patents, referenced in this specification are incorporated herein by reference as though fully set forth.

The invention claimed is:

1. A package for storing a transdermal delivery patch that comprises an active pharmaceutical ingredient and (i) at least one skin penetration enhancer that is a keto acid and at least one additional enhancer that is a long chain monoglyceride or a C8-C16 ester of a short chain carboxylic acid, or (ii) at least one skin penetration enhancer that is a sulfoxide;
  wherein the package is a pouch that fully encloses the transdermal delivery patch and comprises a multilayered packaging film having an article side polymer film that forms the innermost layer of the pouch, wherein the article side polymer film is heat sealable upon itself to effect the full enclosure of the transdermal patch and is selected from a thermoplastic fluoropolymer, amorphous polyethylene terephthalate, or polyacrylonitrile/methyl acrylate-acrylonitrile/butadiene graft copolymer;
  wherein the article side polymer film absorbs less than about 0.5% by weight of the skin penetration enhancer(s) from the patch during a storage period of 6 months or longer at room temperature.

2. The package of claim 1, wherein the transdermal delivery patch to be stored therein comprises the active pharmaceutical ingredient and at least one skin penetration enhancer that is a keto acid and at least one additional enhancer that is a long chain monoglyceride or a C8-C16 ester of a short chain carboxylic acid.

3. The package of claim 2, wherein, in the transdermal delivery patch to be stored therein, the keto acid is levulinic acid (LA), the long chain monoglyceride is glycerol monooleate (GMO), and the C8-C16 ester of a short chain carboxylic acid is lauryl lactate (LL).

4. The package of claim 3, wherein the amount of the first penetration enhancer in the transdermal delivery patch to be stored therein is about 0.5 wt % to about 10 wt % and the amount of the second penetration enhancer in the patch is about 0.5 wt % to about 10 wt %.

5. The package of claim 1, wherein the transdermal delivery patch to be stored therein comprises an active pharmaceutical ingredient, at least one skin penetration enhancer that is a sulfoxide, and at least one additional skin penetration enhancer that is either a C8-C16 ester of a short chain carboxylic acid or a lower alkyl ester of a short chain carboxylic acid.

6. The package of claim 5 wherein, in the transdermal delivery patch to be stored therein, the sulfoxide is dimethyl sulfoxide (DMSO), C8-C16 ester of a short chain carboxylic acid is LL, and the lower alkyl ester of a short chain carboxylic acid is ethyl lactate (EL).

7. The package of claim 5, wherein the enhancers in the transdermal delivery patch to be stored therein comprise DMSO, LL, EL, and a medium chain fatty acid.

8. The package of claim 7, wherein the enhancers in the transdermal delivery patch to be stored therein comprise about 4% to about 12% of DMSO, about 4% to about 13% of LL, about 0.5% to about 2.5% of EL; and about 3% to about 9% of capric acid.

9. The package of claim 1, wherein the transdermal delivery patch to be stored therein comprises a backing layer affixed to an adhesive polymer matrix, wherein the adhesive polymer matrix comprises:
  a. the active pharmaceutical ingredient;
  b. an adhesive polymer; and
  c. (i) a first penetration enhancer selected from the group consisting of a keto acid and a pharmaceutically acceptable salt thereof and a second penetration enhancer selected from the group consisting of long chain monoglycerides and C8-C16 esters of short chain carboxylic acid or
  (ii) a first penetration enhancer selected from the group consisting of alkyl sulfoxides and a second penetration enhancer selected from the group consisting of C8-C16 esters of a short chain carboxylic acid, lower alkyl esters of a short chain carboxylic acid, or both.

10. The package of claim 1, wherein the article side polymer film is an acrylonitrile/methyl acrylate-acrylonitrile/butadiene graft copolymer.

11. The package of claim 1, wherein the article side polymer film is an amorphous polyethylene terephthalate.

12. The package of claim 1, wherein the article side polymer film is a thermoplastic fluoropolymer.

13. The package of claim 1, within which is contained a transdermal delivery patch having a progestin and an estrogen as active pharmaceutical ingredients.

14. The package of claim 13, wherein the progestin is levonorgestrel.

15. The package of claim 13, wherein the estrogen is ethinyl estradiol.

16. An article of manufacture comprising a transdermal delivery patch that includes contraceptive hormones and (i) at least one skin penetration enhancer that is a keto acid and at least one additional enhancer that is a long chain monoglyceride or a C8-C16 ester of a short chain carboxylic acid, or (ii) at least one skin penetration enhancer that is a sulfoxide; wherein the transdermal delivery patch is contained within a package that fully encloses the transdermal delivery patch and comprises a multilayered packaging film having an article side polymer film that forms the innermost layer of the pouch, wherein the article side polymer film is heat sealable upon itself to effect the full enclosure of the transdermal patch and is selected from thermoplastic fluoropolymer, amorphous polyethylene terephthalate, or polyacrylonitrile/methyl acrylate-acrylonitrile/butadiene graft copolymer; wherein the article side polymer film absorbs less than about 0.5% by weight of the skin penetration enhancer(s) from the patch during a storage period of 6 months or longer at room temperature.

17. The article of manufacture of claim 16, wherein the contraceptive hormones include a progestin and an estrogen.

18. The article of manufacture of claim 17, wherein the progestin is levonorgestrel.

19. The article of manufacture of claim 18, wherein the estrogen is ethinyl estradiol.

* * * * *